United States Patent
Stetson et al.

(10) Patent No.: US 9,498,618 B2
(45) Date of Patent: *Nov. 22, 2016

(54) MEDICAL CABLE CONNECTOR FOR A MEDICAL LEAD PROVIDING AN ELECTRICAL RECEPTACLE THAT IS MOVABLE RELATIVE TO AN OUTER BODY

(71) Applicant: MEDTRONIC, INC., Minneapolis, MN (US)

(72) Inventors: Daniel J. Stetson, Blaine, MN (US); Carole A. Tronnes, Stillwater, MN (US); David W. Lee, Apple Valley, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/617,934

(22) Filed: Feb. 10, 2015

(65) Prior Publication Data
US 2015/0151110 A1 Jun. 4, 2015

Related U.S. Application Data

(63) Continuation of application No. 13/069,077, filed on Mar. 22, 2011, now Pat. No. 8,954,163.

(60) Provisional application No. 61/319,804, filed on Mar. 31, 2010.

(51) Int. Cl.
| | | |
|---|---|---|
| A61N 1/375 | (2006.01) |
| A61N 1/05 | (2006.01) |
| H01R 13/516 | (2006.01) |
| H01R 24/58 | (2011.01) |
| H01R 4/00 | (2006.01) |
| H01R 43/26 | (2006.01) |
| H01R 13/453 | (2006.01) |

(52) U.S. Cl.
CPC ............ *A61N 1/05* (2013.01); *H01R 4/00* (2013.01); *H01R 13/516* (2013.01); *H01R 24/58* (2013.01); *H01R 43/26* (2013.01); *H01R 13/4538* (2013.01); *H01R 2201/12* (2013.01); *Y10T 29/49174* (2015.01)

(58) Field of Classification Search
CPC .................................. A61N 1/04; H01R 4/00
See application file for complete search history.

(56) References Cited

U.S. PATENT DOCUMENTS

| | | | |
|---|---|---|---|
| 5,241,957 A * | 9/1993 | Camps ................ | A61N 1/0551 607/119 |
| 2007/0050005 A1 * | 3/2007 | Lauro ..................... | A61N 1/05 607/126 |

* cited by examiner

*Primary Examiner* — Joseph Dietrich
(74) *Attorney, Agent, or Firm* — Withers & Keys, LLC (57) ABSTRACT

A medical cable connector of a medical cable receives a medical lead while an electrical receptacle within the medical cable connector is placed into a distal position relative to an outer body of the medical cable connector. The electrical receptacle is retracted to a proximal position once insertion of the medical lead into the medical cable connector is completed. The electrical receptacle may be mounted to an inner body which moves relative to the outer body. A biasing member may be present to bias the inner body to a particular position. A slider may be present to provide a clinician with a surface to touch when applying force to position the electrical receptacle in the distal position for insertion of the medical lead. Various other features may be present to facilitate insertion of the medical lead and/or to maintain the position of the electrical receptacle relative to the outer body.

26 Claims, 9 Drawing Sheets

MEDICAL CABLE CONNECTOR FOR A MEDICAL LEAD PROVIDING AN ELECTRICAL RECEPTACLE THAT IS MOVABLE RELATIVE TO AN OUTER BODY

RELATED APPLICATIONS

This patent application claims priority to U.S. Provisional Patent Application No. 61/319,804, filed Mar. 31, 2010, the entire disclosure of which is being expressly incorporated herein by reference.

TECHNICAL FIELD

Embodiments relate to cable connectors that receive proximal ends of medical leads. More particularly, embodiments relate to cable connectors that provide electrical receptacles to receive electrical conductors of the medical leads where the electrical receptacles are movable within an outer body of the cable connector.

BACKGROUND

External medical devices such as those being used for trial stimulation periods include a cable extending from the medical device to an area that is external to the body of a patient and nearby the site of implantation of a medical stimulation lead. The cable includes a cable connector on a distal end. This cable connector includes an electrical receptacle that receives an electrical conductor such as a pin present on the proximal end of the medical stimulation lead. The proximal end of the medical stimulation lead is also present in the area nearby the site of implantation.

The medical stimulation lead has a distal end present within the body at the stimulation site where an electrode provides the stimulation from the medical device. The electrode is connected to the electrical conductor pin present on the proximal end by including an intermediate conductor that is surrounded by an insulator forming a lead body. The lead body and intermediate conductor are flexible which allows the medical stimulation lead to be routed to the stimulation site during implant and allows the lead to flex during movement by the patient.

When completing the installation of the medical device, the clinician must insert the electrical conductor pin of the medical stimulation lead into the cable connector. The electrical conductor pin is typically more rigid than the intermediate conductor and lead body, so the clinician may grasp the electrical conductor pin to perform the insertion. However, most or all of the electrical conductor pin will be inserted into the housing of the cable connector, Therefore, once some portion of the electrical conductor pin has been inserted, the clinician becomes unable to grasp the lesser amount of the electrical conductor pin that remains outside of the cable connector. Grasping the lead body near the proximal end of the medical stimulation lead provides little help in completing the insertion of the medical stimulation lead due to the flexible nature of the lead body and intermediate conductor. Therefore, the clinician may struggle to complete the insertion of the electrical conductor pin and may resort to uncomfortable and potentially harmful techniques by using a fingernail to press against the distal end of the electrical conductor pin and/or a tool to grasp the distal end, which may cause damage to the lead.

SUMMARY

Embodiments address issues such as these and others by providing a cable connector that includes an electrical receptacle that can be moved to a more distal location within an outer body of the cable connector. The electrical receptacle may be mounted on an inner body that is contained within the outer body where the inner body is movable in a longitudinal direction to provide movement of the electrical receptacle. During insertion of the medical lead, the receptacle may be moved closer to a distal end of the outer body where the medical lead is introduced. Upon the electrical conductor of the medical lead engaging the electrical receptacle, the electrical receptacle may then be retracted to a more proximal location within the outer body.

Embodiments provide a method of attaching a medical lead having at least a first electrical conductor exposed on a proximal end to a cable connector. The method involves providing the cable connector having an outer body defining a longitudinal axis and with an opening at a distal end, an inner body contained within the outer body while being movable along the longitudinal axis and having at least a first electrical receptacle. The method further involves moving the inner body to a distal position within the outer body. While the inner body is in the distal position, the proximal end of the first electrical conductor is inserted into the opening at the distal end of the outer body and into the first electrical receptacle of the inner body. After the proximal end of the first electrical conductor is inserted into the first electrical receptacle of the inner body, then the inner body including the electrical receptacle and proximal end of the electrical conductor is moved to a proximal position within the outer body.

Embodiments provide a medical cable connector that includes an outer body defining a longitudinal axis with an opening at a distal end and with an aperture. The medical cable connector includes an inner body contained within the outer body while being movable along the longitudinal axis. The medical cable connector also includes a first electrical receptacle mounted to the inner body and contained within the outer body.

Embodiments provide a medical system that includes a medical device containing electrical circuitry that produces stimulation signals at an output. The medical system further includes a medical cable including at least one electrical conductor surrounded by an insulator, the medical cable including a proximal end where the electrical conductor is electrically connected to the output of the medical device and including a distal end. Additionally, the medical system includes a medical cable connector present at the distal end of the medical cable, and the medical cable connector includes an outer body defining a longitudinal axis and with an opening at a distal end. The medical cable connector further includes an inner body contained within the outer body while being movable along the longitudinal axis. The medical cable connector also includes an electrical receptacle mounted to the inner body and contained within the outer body, with the electrical receptacle being electrically connected to the electrical conductor of the medical cable.

DETAILED DESCRIPTION

Embodiments provide for a medical cable connector that includes an electrical receptacle that receives an electrical conductor of a medical lead while allowing the electrical receptacle to be moved between a distal position and a proximal position in relation to an outer body surrounding the electrical receptacle. In this manner, the electrical conductor may be inserted into the electrical receptacle with the electrical receptacle in the distal position and then the electrical receptacle may be retracted to the proximal position.

Figure 1:
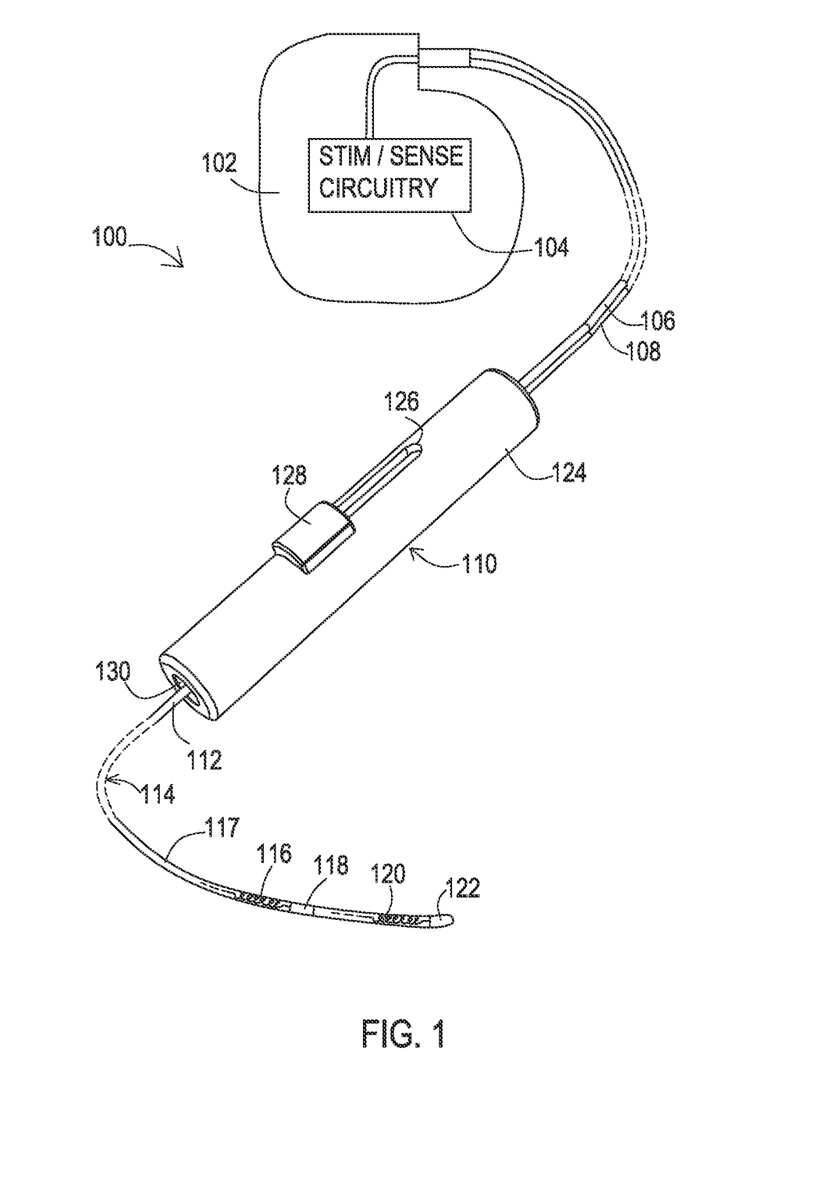
FIG. 1 shows an example of a medical system including a medical device, associated medical cable and implantable medical lead as well as a medical cable connector according to various embodiments.

FIG. 1 shows one example of a medical system that includes a medical device 102. The medical device 102 may be of various types, such as a pulse generator and/or a physiological sensing device and may be for purposes such as cardiovascular or neurological therapies. The medical device 102 includes circuitry 104 that may be used to perform the stimulation or sensing functions.

The medical device 102 includes one or more medical cables 106, 108 to transfer electrical signals such as stimulation signals or sensed signals. As shown, the medical device 102 is bipolar and provides two medical cables 106, 108 with each having one electrical conductor surrounded by an insulator. It will be appreciated that other numbers of electrical conductors may be used for different configurations and therapies being provided by the medical device 102. It will be further appreciated that the individual electrical conductors may be contained within one insulative body rather than having a separate cable 106, 108 for each electrical conductor.

The medical cables 106, 108 lead to one or more medical cable connectors 110. In the example shown, both cables 106, 108 lead to a single bi-polar medical cable connector 110. However, the medical cable connector according to embodiments disclosed herein may be unipolar or multi-polar.

The medical cable connector 110 provides an outer body 124 that may be constructed of a variety of materials such as polymeric materials like polycarbonate or polypropylene. The outer body 124 has an open proximal end to allow the medical cables 106, 108 to pass through and also defines an opening 130 on a distal end. The opening 130 allows an electrical conductor end 112 of an implantable medical lead 114 to pass through. In this example, the outer body includes an aperture 126 that allows a slider 128 to move longitudinally. The movement of the slider 128, which may be also be constructed of a variety of materials such as polymeric materials polycarbonate or polypropylene, allows a clinician to move the slider 128 to a distal position during insertion of the electrical conductor end 112 and to move the slider 128 to a proximal position after insertion to pull the electrical conductor end 112 into the cable connector 110. After proper insertion of the electrical conductor end 112, the cable connector 110 may be taped or otherwise fixed to the skin of the patient.

The implantable medical lead 114 includes one or more electrodes 118, 122 on a distal end. An intermediate electrical conductor 116, 120 that is covered by an insulative lead body 117 is present for each electrode 118, 122 and carries signals between electrical conductors in the electrical conductor end 112 forming the proximal end of the medical lead 114 and the electrodes 118, 122.

The electrical conductor end 112 may be significantly stiffer than the portion of the medical lead 114 where the intermediate electrical conductors 116, 120 and insulative lead body 117 are present. This stiffness of the electrical conductor end 112 allows a clinician to grasp the electrical conductor end 112 and insert it into the cable connector 110 by pushing it in the proximal direction. The flexibility of the remainder of the medical lead 114 allows it to be routed to the stimulation site and flex during movement by the patient. The outer surface of the electrical conductor end 112 may be constructed of various materials such as polyester tubing. While in this example the outer surface of the electrical conductor end 112 may be constructed of a pliable material, conductors 150 and 156, which are discussed below in relation to FIGS. 4 and 5, within the electrical conductor end 112 may be constructed of a rigid conductive material like stainless steel to facilitate insertion. In other embodiments, the electrical conductor end 112 may be constructed of rigid materials as well.

Figure 2:
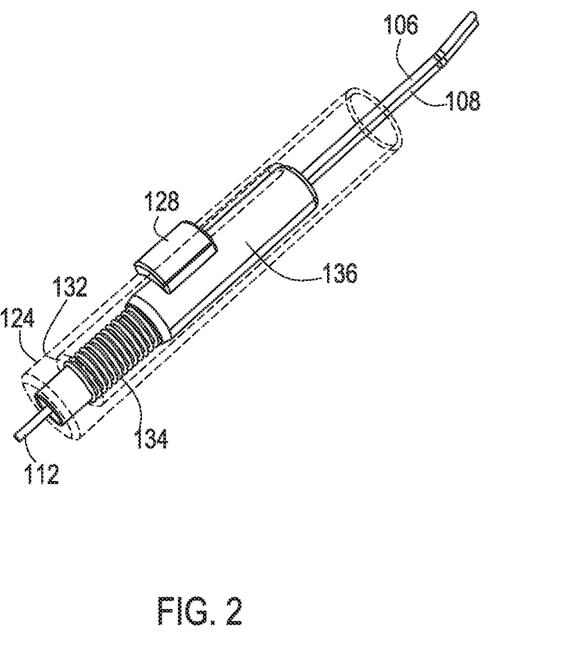
FIG. 2 shows the medical cable connector according to various embodiments with an outer body shown transparently to reveal an inner body and a biasing member.
Figure 3:
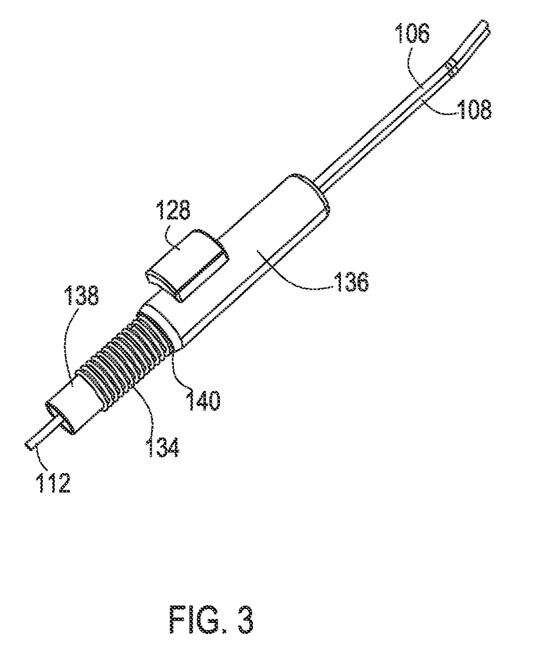
FIG. 3 shows the inner body and biasing member of the medical cable connector according to various embodiments.

FIG. 2 shows a view of the medical cable connector 110 with the outer body 124 shown transparently so that the relationship of the outer body 124 to an inner body 136 can be seen. The inner body 136 may be constructed of various materials such as polymeric materials like polycarbonate or polypropylene. FIG. 3 shows the medical cable connector 110 with the outer body 124 removed so that the inner body 136 can be seen without obstruction.

The outer body 124 includes a section where the opening 130 has a small diameter that terminates at an abutment 132 where the diameter is larger. The inner body 136 includes a smaller diameter distal portion 138 that extends to an abutment 140 where the diameter of the inner body 136 increases. The smaller diameter distal portion 138 passes through the smaller diameter distal opening 130 of the outer body 124 while the larger diameter proximal portion of the inner body 136 resides within the larger diameter distal portion of the opening 130.

This relationship between the inner body 136 and the outer body 124 allows the inner body 136 to be contained within the outer body 124 yet be movable relative to the outer body 124 along a longitudinal axis of the outer body 124. The clinician may apply pressure via a thumb or other finger to the slider 128 which is attached to the inner body 136. The slider 128 is confined by the aperture 126 of the outer body 124 which allows the slider 128 to move in the longitudinal direction to thereby move the inner body 136.

In some embodiments, a biasing member such as a spring 134 may be included to bias the inner body 136 relative to the outer body 124. In the example shown, the spring 134 is a coil spring that is present between the abutment 132 of the outer body 124 and the abutment 140 of the inner body 136.

The coil spring 134 biases the inner body 136 into a proximal or retracted position within the outer body 124. Thus, the inner body 136 may be forced into the distal position for insertion of the electrical conductor end 112 by pressing the slider 128 in the distal direction. The inner body 136 may then be moved into the proximal position to retract the electrical conductor end 112 into the outer body 124 by releasing the slider 128 and allowing the spring 134 to force the inner body 136 in the proximal direction.

Figure 4:
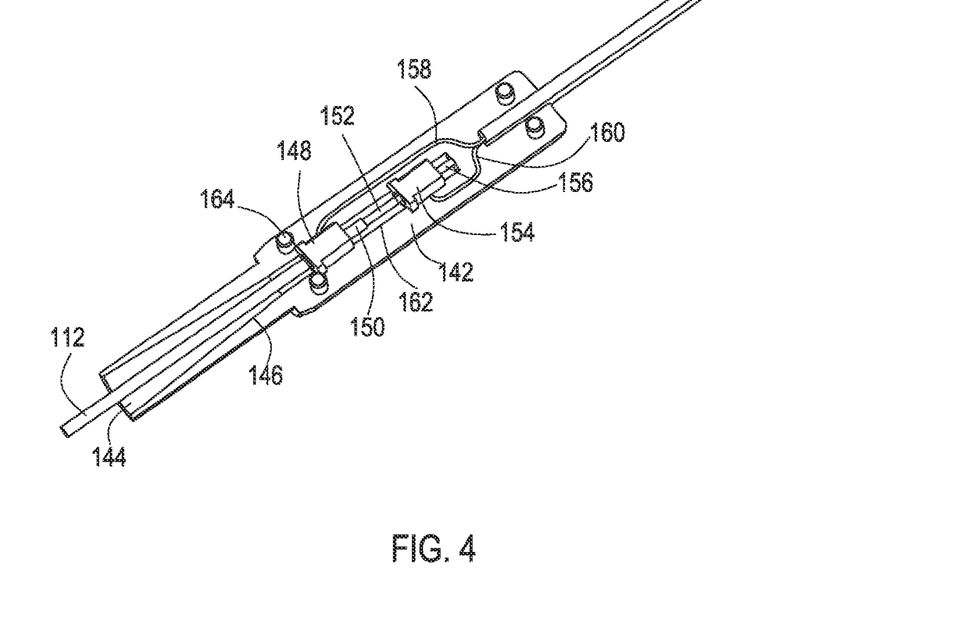
FIG. 4 shows the interior of the inner body of the medical cable connector according to various embodiments.

FIG. 4 shows one half of the inner body 136 to reveal the passageway 144 of the inner body 136. This passageway leads to the location of the one or more electrical receptacles that receive the one or more exposed conductors of the electrical conductor end 112. In this particular example, the passageway 144 has a tapered surface 146 that guides the electrical conductor end 112 as it is inserted. The distal opening of the passageway 144 can therefore be larger in diameter than the opening at the electrical receptacles to make inserting the electrical conductor end 112 into the distal end of the passageway 144 easier.

In this example of FIG. 4, the electrical receptacles are contained within electrical receptacle housings 148, 154 but it will be appreciated that the electrical receptacles may be shaped so as to be mounted to the inner body 136 without the need for electrical receptacle housings. These housings 148, 154 may be constructed of various rigid materials such as nickel. In this bipolar example, the housings 148, 154 are axially spaced along the longitudinal axis of the inner body 136, with the axial spacing being appropriate to accommodate the axial spacing between the two exposed electrical conductors 150, 156 of the electrical conductor end 112. As shown, the electrical conductor 150 and the electrical conductor 156 are concentric with the electrical conductor 150 having the larger diameter. An insulative layer 152 is present between the two electrical conductors 150, 156 and extends beyond the electrical conductor 150 in the proximal direction.

Electrical conductors 158, 160 extend from each electrical receptacle housing 148, 154 and continue into the medical cables 106, 108. The electrical conductors 158, 160 may reside within channels formed in the inner body 136 that route the electrical conductors 158, 160 from the electrical receptacle housings 148, 154 to the medical cables 106, 108.

In this particular example, the inner body 136 may be constructed of two halves with one half 142 being shown in FIG. 4. During assembly, the electrical receptacle housings 148, 154 and electrical conductors 158, 160 may be put into proper position and then the second half of the inner body 136 is joined to the first half 142. One manner of joining the two halves of the inner body 136 is to include protrusions 164 on one half and holes in the other half that receive the protrusions 164. Interference fit, adhesives, and the like may be used to secure the two halves.

Figure 5:
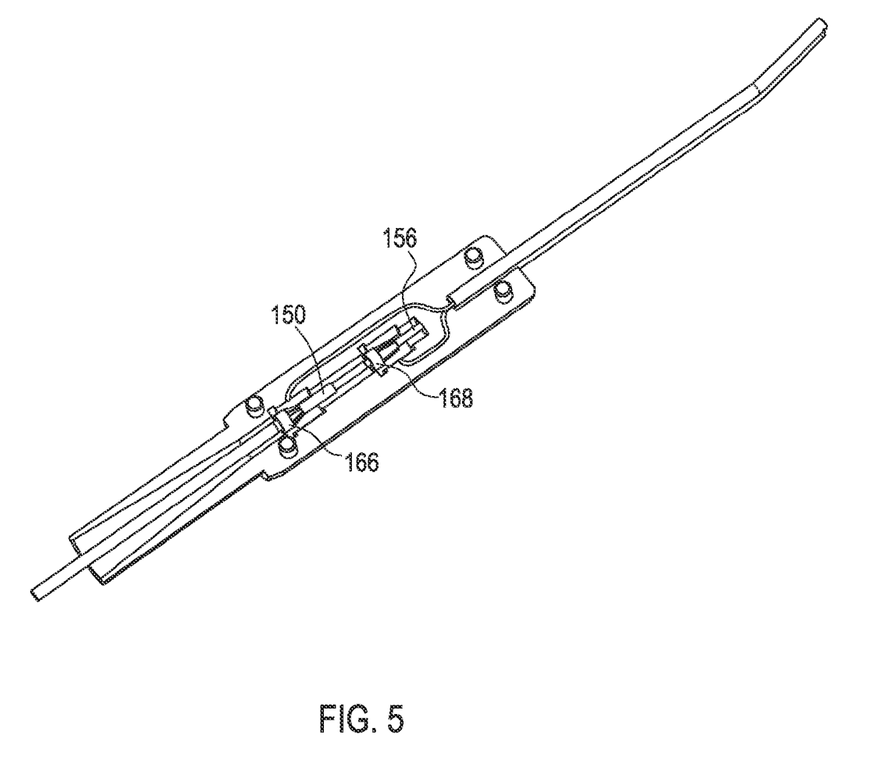
FIG. 5 shows electrical receptacles present within the inner body of the medical cable connector according to various embodiments.

FIG. 5 shows the half of the inner body 136 with the electrical receptacle housings 148, 154 removed to reveal the electrical receptacles 166, 168. In this particular example, the electrical receptacles are ring shaped with inward angled fingers that spring open as the electrical conductor 150, 1156 passes through. The inward angled fingers are biased inward so as to sustain adequate physical and electrical contact with the electrical conductors 150, 156. It will be appreciated that other electrical receptacle shapes and designs are also applicable. The electrical receptacles 166, 168 themselves are conductive and may be constructed of various conductive materials such as beryllium copper to conduct electrical signals between the exposed electrical conductors 150, 156 and the electrical conductors 158, 160.

As shown for this bipolar example, the electrical receptacles 166, 168 are encountered sequentially during insertion. The first electrical conductor 156 to enter the passageway 144 encounters the more distal electrical receptacle 166. The first electrical conductor 156 passes through the electrical receptacle 166 and continues onward in the proximal direction until reaching the more proximal electrical receptacle 168. The second electrical conductor 150 reaches the more distal electrical receptacle 166 when the first electrical conductor 156 has reached the more proximal electrical receptacle 168.

Figure 6:
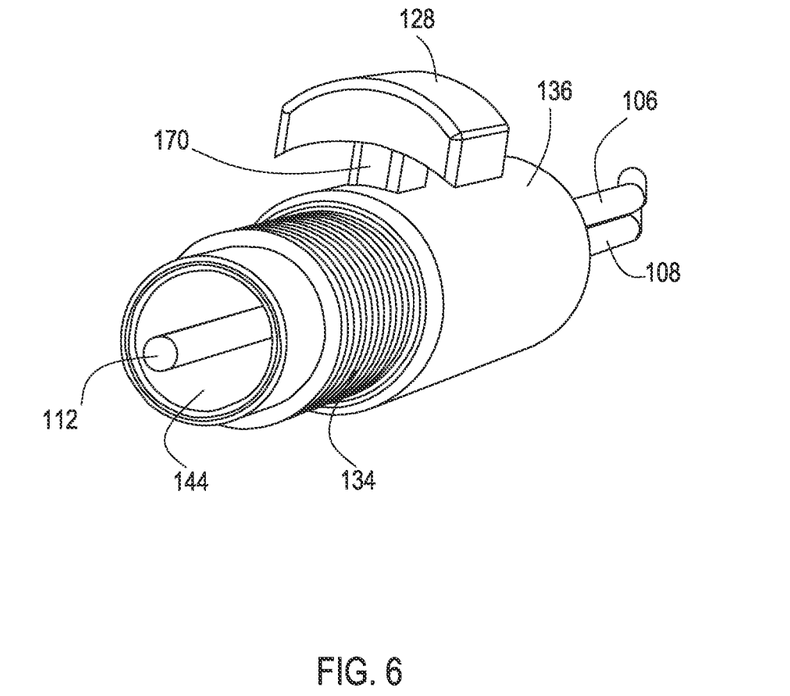
FIG. 6 shows a distal end view of the inner body and a slider of the medical cable connector according to various embodiments.

FIG. 6 shows a distal end view of the inner body 136. This view illustrates the attachment of the slider 128 to the inner body 136 in this particular example. The slider of this example includes a post 170 which mounts to the inner body 136. For instance, the inner body 136 may have an aperture that the post 170 resides within. The post 170 passes through the aperture 126 of the outer body 124. While this view shows the slider 128 attached to the inner body 136 without the outer body 124 present, this is for purposes of illustration. The inner body 136 may be installed within the outer body 124 prior to attachment of the slider 128 if the outer body 124 is constructed as one piece. However, for embodiments where the outer body 124 is constructed of two halves, the slider 128 may be attached to the inner body 136 before insertion into the outer body 124 and/or may be constructed as an integral portion of the inner body 136.

Figure 7:
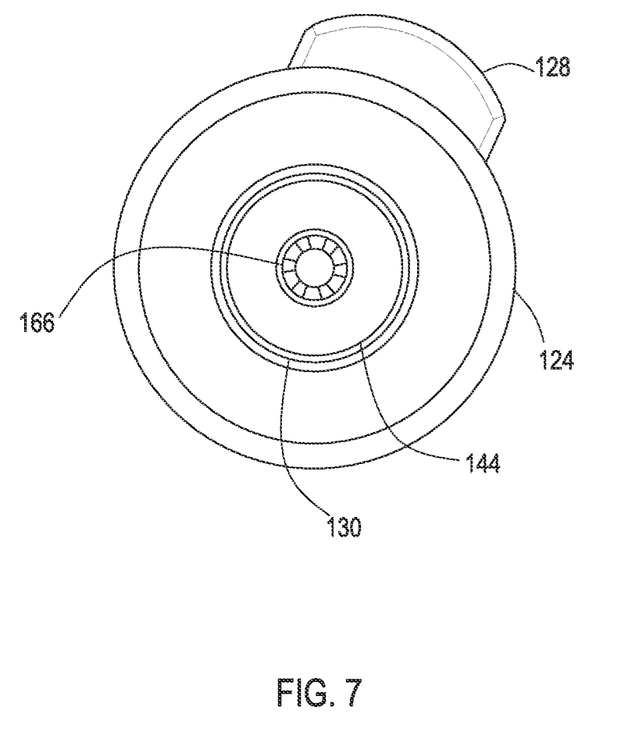
FIG. 7 shows a distal end view of the medical cable connector prior to insertion of the electrical conductor of the implantable medical lead.

FIG. 7 shows a distal end view of the cable connector 110 where the relationship between the opening 130 of the outer body 124, the tapered passageway 144 of the inner body 136, and the electrical receptacle 166 can be seen. This view illustrates that the relative sizes of the opening 130, the opening at the distal end of the passageway 144, and the electrical receptacle 166 facilitate the insertion of the electrical conductor end 112. While the distal end of the inner body 136 is approximately flush with the distal end of the outer body 124 while in the distal position in this embodiment, it will be appreciated that other embodiments may provide for the distal end of the inner body 136 to extend distally beyond the distal end of the outer body 124 or to not extend all the way to the distal end of the outer body 124 when in the distal position.

Furthermore, the opening 130 of the outer body 124 may be smaller in diameter than the distal end of the tapered passageway 144. A result of this configuration is that the distal end of the tapered passageway 144 is obstructed in the distal direction upon the distal end of the tapered passageway 144 approaching the opening 130. The interior surface of the outer body 124 forming the opening 130 thereby provides a stop for distal movement of the inner body 136 relative to the outer body 124. This stop for distal movement may be in addition to or as an alternative to a stop being provided by contact of the post 170 with the distal end of the aperture 126.

Figure 8:
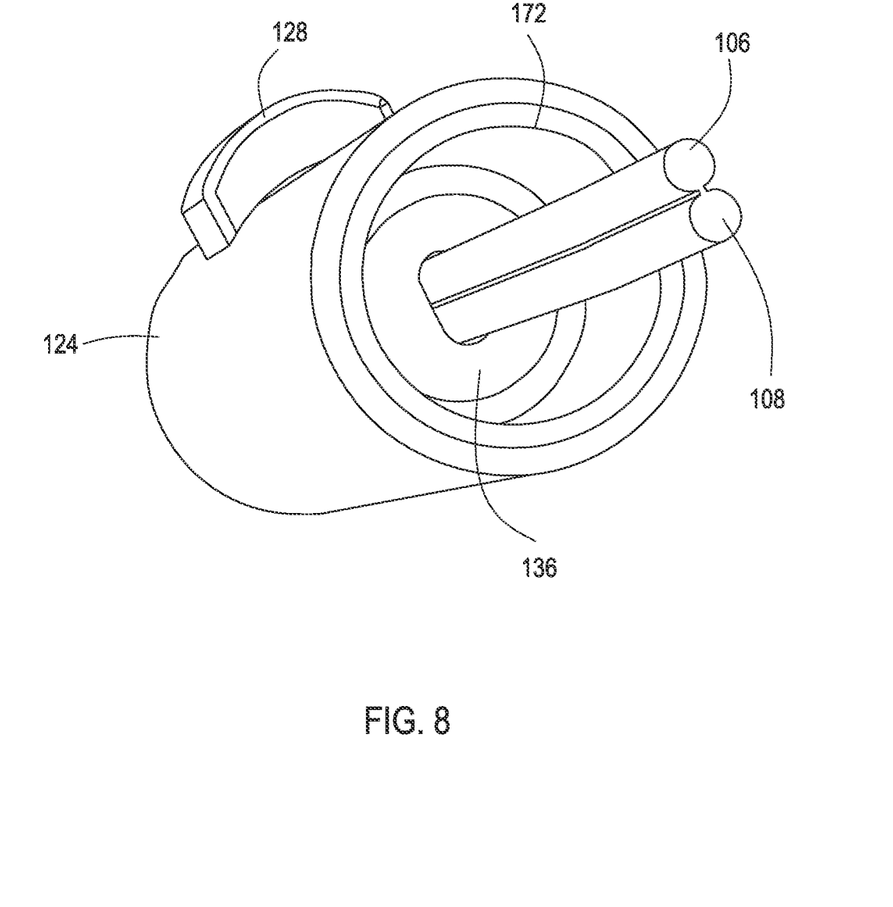
FIG. 8 shows a proximal end view of the medical cable connector according to various embodiments.

FIG. 8 shows a proximal end view of the cable connector 110 where the relationship between the inner body 136, outer body 124, and medical cables 106, 108 can be seen. A proximal end opening 172 in the outer body 124 allows for ease of insertion of the inner body 136. While the proximal end of the inner body 136 may be approximately flush with the proximal end of the outer body 124 while in the proximal position in this embodiment, it will be appreciated that other embodiments may provide for the proximal end of the inner body 136 to extend proximally beyond the proximal end of the outer body 124 or to not extend all the way to the proximal end of the outer body 124 when in the proximal position.

Figure 9:
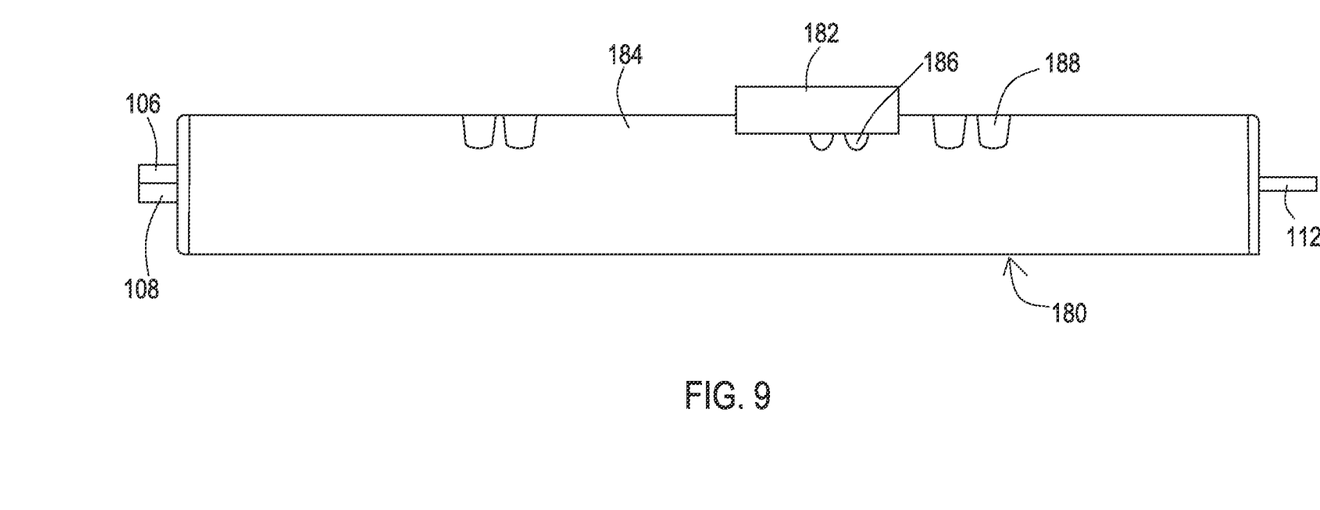
FIG. 9 shows a side view that illustrates protrusions on the slider and detents within the outer body of the medical cable connector according to various embodiments.

FIG. 9 shows a side view of an embodiment of a medical cable connector 180 that provides additional features to secure the position of the inner body 136, and hence the electrical receptacles 166, 168, relative to the outer body 184. These features include one or more protrusions 186 on the underside of the slider 182 as well as one or more detents 188 formed in the outer body 184 that receive the protrusions 186. Accordingly, when the slider 82 is moved to the proximal or distal extremes, the protrusions 186 engage the detents 188 to hold the slider in the particular position. This relieves the clinician from maintaining the slider 128 in the distal position during insertion of the electrical conductor end 112 and also relieves the spring or other biasing member from being the sole manner of maintaining the slider 128 in the proximal position after insertion.

In some embodiments, the biasing member may be omitted in favor of relying on the engagement of the protrusions 186 with the detents 188 to hold the slider 182, and hence the inner body 136, in a given position. Furthermore, FIG. 9 shows detents 188 for both the distal and proximal positions. It will be appreciated that detents 188 may be used for only one of those positions rather than both. For instance, an embodiment may rely on the clinician to hold the slider 182 in the distal position during insertion while relying on the detents 188 on the proximal side to hold the slider 182 in the proximal position after insertion. As another example, an embodiment may rely on the detents to hold the slider 182 in the distal position during insertion while relying on the spring to hold the slider 182 in the proximal position after insertion.

The example of FIG. 9 provides the protrusions 186 on the slider 182 and the detents within the outer body 184, These features may be reversed for some embodiments, where the underside of the slider 192 may include detents and the outer body 184 may provide protrusions that engage the detents of the slider 182 to hold the slider 182 in a particular longitudinal position.

Figure 10:
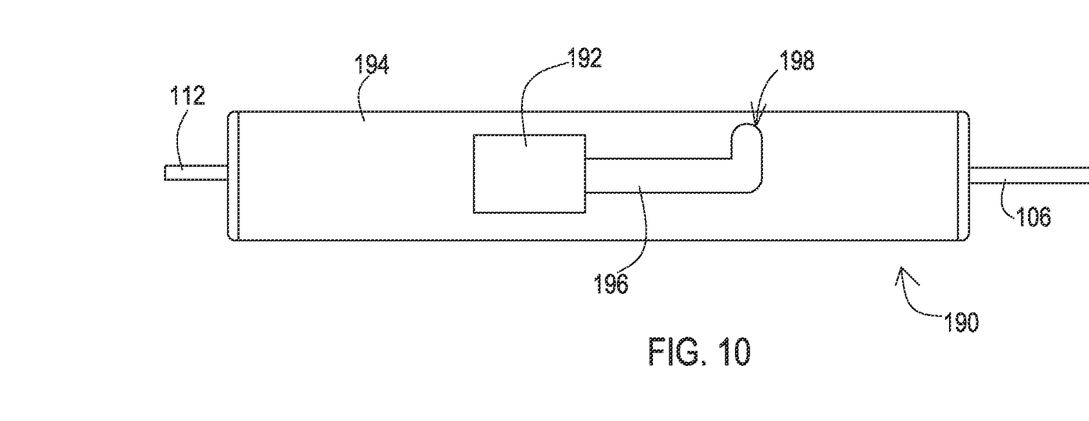
FIG. 10 shows atop view that illustrates an aperture and a locking slot within the outer body of the medical cable connector according to various embodiments.

FIG. 10 shows a top view of an embodiment of a medical cable connector 190 that provides other additional features to secure the position of the inner body 136, and hence the electrical receptacles 166, 168, relative to the outer body 194. These features include one or more slots 198 formed with the longitudinal aperture 196 of the outer body 194, with the slot diverging at an angle from the longitudinal axis of the aperture 196. The angle is severe enough so that when the post 170 of the slider 192 is forced, the post 170 will enter and reside within the slot 198 to hold the slider 192, and hence the inner body 136, in that particular position. In the example shown, the angle is 90 degrees but other angles are also applicable to hold the slider 192 in the particular longitudinal position.

As the inner body 136 is cylindrical and the interior surface of the outer body 194 is also cylindrical, the inner body 136 is contained while being free to move longitudinally and while also being free to rotate within the outer body 194 so long as the post 170 of the slider 192 is not obstructed. The post 170 is obstructed by the aperture 196 to prevent rotation except when positioned along the aperture 196 at the slot 198.

In the example shown, the slot 198 is located at the proximal end to hold the slider 192 in the proximal position. The slot 198 may be used in conjunction with the spring to hold the slider 192 and inner body 136 in the proximal position or may be used alone for embodiments where the spring is omitted. Furthermore, the slot 198 may also be located on the distal end of the aperture 196, in addition to being located on the proximal end, to hold the slider 192 in the distal position during insertion. In another example, the slot 198 may be located on the distal end rather than being located on the proximal end so that the slot 198 holds the slider 192 in the distal position during insertion while the biasing member holds the slider 192 in the proximal position after insertion.

While embodiments have been particularly shown and described, it will be understood by those skilled in the art that various other changes in the form and details may be made therein without departing from the spirit and scope of the invention.

What is claimed is:

1. A method of attaching a medical lead having at least a first electrical conductor exposed on a proximal end to a medical cable connector, comprising:
   providing the medical cable connector having an outer body defining a longitudinal axis and with an opening at a distal end, an inner body contained within the outer body while being movable along the longitudinal axis and having at least a first electrical receptacle;
   moving the inner body to a distal position within the outer body;
   while the inner body is in the distal position, inserting the proximal end of the first electrical conductor into the opening at the distal end of the outer body and into the first electrical receptacle of the inner body; and
   after the proximal end of the first electrical conductor is inserted into the first electrical receptacle of the inner body, then moving the inner body including the electrical receptacle and proximal end of the electrical conductor to a proximal position within the outer body.

2. The method of claim 1, wherein the medical cable connector further comprises a slider attached to the inner body and exposed through an aperture in the outer body while being movable along the longitudinal axis, the method further comprising:
   moving the slider relative to the aperture to move the inner body to the distal position; and
   moving the slider relative to the aperture to move the inner body the proximal position.

3. The method of claim 2, wherein the medical cable connector further has a biasing member positioned to bias the inner body toward the proximal position, wherein moving the slider to move the inner body to the distal position comprises applying a force to the slider that opposes the biasing member, and wherein moving the slider to move the inner body to the proximal position comprises releasing the force to allow the biasing member to return the inner body to the proximal position.

4. The method of claim 3, wherein the outer body includes an abutment and wherein the inner body includes an abutment, wherein the biasing member is a coil spring with a distal end contacting the abutment of the outer body and with a proximal end contacting the abutment of the inner body.

5. The method of claim 2, wherein moving the slider to move the inner body to the distal position comprises applying a force to the slider in a direction toward the distal position, and wherein moving the slider to move the inner body to the proximal position comprises applying a force to the slider in a direction toward the proximal position.

6. The method of claim 1, wherein the medical cable connector comprises a second electrical receptacle axially spaced from the first electrical receptacle on the inner body, wherein the medical lead includes a second electrical conductor exposed on the proximal end and axially spaced from the first electrical conductor exposed on the proximal end, and wherein inserting the proximal end of the first electrical conductor into the opening at the distal end of the outer body and into the first electrical receptacle of the inner body comprises passing the first electrical conductor through the second electrical receptacle prior to the first electrical conductor reaching the first electrical receptacle.

7. The method of claim 2, wherein the outer housing includes detents and wherein the slider includes protrusions, the method further comprising placing the protrusions into the detents to hold the inner body in a fixed relationship to the outer body.

8. The method of claim 2, wherein the aperture of the outer housing includes a longitudinal axis and further includes a slot angled relative to the longitudinal axis, the method further comprising moving the slider into the slot to hold the inner body in a fixed relationship to the outer body.

9. The method of claim 1, wherein the proximal end of the medical lead is more rigid than a remainder of the medical lead, the method further comprising grasping an area of the more rigid proximal end until inserting the medical lead is completed.

10. A medical cable connector, comprising:
an outer body defining a longitudinal axis and with an opening at a distal end;
an inner body contained within the outer body while being movable along the longitudinal axis; and
a first electrical receptacle mounted to the inner body and contained within the outer body; and
a second electrical receptacle mounted to the inner body and spaced in the direction of the longitudinal axis from the first electrical receptacle on the inner body.

11. The medical cable connector of claim 10, wherein the outer body includes an aperture, the cable connector further comprising:
a slider attached to the inner body and exposed through the aperture in the outer body while being movable along the longitudinal axis, the slider positioning the inner body and the electrical receptacle within the outer body.

12. The medical cable connector of claim 11, further comprising:
a biasing member positioned to bias the inner body toward a proximal position, and wherein the slider is movable against the bias to move the inner body to a distal position.

13. The medical cable connector of claim 12, wherein the outer body includes an abutment and wherein the inner body includes an abutment, wherein the biasing member is a coil spring with a distal end contacting the abutment of the outer body and with a proximal end contacting the abutment of the inner body.

14. The medical cable connector of claim 11, wherein the outer body includes detents and wherein the slider includes protrusions such that when the protrusions are placed into the detents the inner body is held in a fixed relationship to the outer body.

15. The medical cable connector of claim 11, wherein the aperture of the outer body includes a longitudinal axis and further includes a slot angled relative to the longitudinal axis such that when the slider is moved into the slot the inner body is held in a fixed relationship to the outer body.

16. The medical cable connector of claim 10, wherein the inner body includes a passageway from a distal end to the first electrical receptacle, the passageway being tapered from the distal end to an area in closer proximity to the first electrical receptacle.

17. A medical system, comprising:
a medical device containing electrical circuitry that produces stimulation signals;
a medical cable including at least one electrical conductor surrounded by an insulator, the medical cable including a proximal end where the electrical conductor is electrically connected to the electrical circuit of the medical device and including a distal end;
a medical cable connector present at the distal end of the medical cable, the medical cable connector comprising:
an outer body defining a longitudinal axis and with an opening at a distal end; an inner body contained within the outer body while being movable along the longitudinal axis; and
an electrical receptacle mounted to the inner body and contained within the outer body, the electrical receptacle being electrically connected to the electrical conductor of the medical cable.

18. The medical system of claim 17, wherein the outer body includes an aperture, the cable connector further comprising:
a slider attached to the inner body and exposed through the aperture in the outer body while being movable along the longitudinal axis, the slider positioning the inner body and the electrical receptacle within the outer body.

19. The medical system of claim 18, wherein the medical cable connector further comprises:
a biasing member positioned to bias the inner body toward a proximal position, and wherein the slider is movable against the bias to move the inner body to a distal position.

20. The medical system of claim 19, wherein the outer body includes an abutment and wherein the inner body includes an abutment, wherein the biasing member is a coil spring with a distal end contacting the abutment of the outer body and with a proximal end contacting the abutment of the inner body.

21. The medical system of claim 17, further comprising a second electrical receptacle axially spaced from the first electrical receptacle on the inner body.

22. The medical system of claim 18, wherein the outer housing includes detents and wherein the slider includes protrusions such that when the protrusions are placed into the detents the inner body is held in a fixed relationship to the outer body.

23. The medical system of claim 18, wherein the aperture of the outer housing includes a longitudinal axis and further includes a slot angled relative to the longitudinal axis such that when the slider is moved into the slot the inner body is held in a fixed relationship to the outer body.

24. The medical system of claim 17, wherein the inner body includes a passageway from a distal end to the first electrical receptacle, the passageway being tapered from the distal end to an area in proximity to the first electrical receptacle.

25. The medical system of claim 17, further comprising a medical lead having a first electrical conductor exposed on a proximal end of the medical lead, having an electrode located on a distal end of the medical lead, and having an intermediate electrical conductor that interconnects the first electrical conductor and the electrode and that is surrounded by an insulator.

26. The medical system of claim 25, wherein the proximal end of the medical lead is more rigid than the intermediate electrical conductor surrounded by the insulator, wherein the first electrical conductor is present within the first electrical receptacle while at least a portion of the proximal end of the medical lead is outside of the outer housing when the inner body and the electrical receptacle are at a distal position within the outer body, and wherein the first portion of the first electrical conductor is present within the first electrical receptacle while the portion of the proximal end of the medical lead is inside of the outer housing when the inner body and the electrical receptacle are at a proximal position within the outer body.

\* \* \* \* \*